United States Patent [19]

Cabrera et al.

[11] Patent Number: 5,356,752
[45] Date of Patent: Oct. 18, 1994

[54] COMPOUNDS WITH ACID-LABILE PROTECTIVE GROUPS USEFUL IN POSITIVE-WORKING RADIATION-SENSITIVE MIXTURES

[75] Inventors: Ivan Cabrera, Gross-Gerau; Walter Spiess, Dieburg; Georg Pawlowski, Wiesbaden, all of Fed. Rep. of Germany

[73] Assignee: Hoechst Aktiengesellschaft, Frankfurt am Main, Fed. Rep. of Germany

[21] Appl. No.: 920,848

[22] Filed: Jul. 28, 1992

[30] Foreign Application Priority Data

Jul. 31, 1991 [DE] Fed. Rep. of Germany ....... 4125258

[51] Int. Cl.$^5$ ............................................. G03C 1/492
[52] U.S. Cl. ................................... 430/270; 430/326
[58] Field of Search ................................ 430/270, 326

[56] References Cited

U.S. PATENT DOCUMENTS 4,983,501  1/1991  Ruckert ............................. 430/326
5,069,997  12/1991  Schwalm et al. .................... 430/270

FOREIGN PATENT DOCUMENTS 0031566  7/1981  European Pat. Off. .
2342068  4/1974  Fed. Rep. of Germany .

OTHER PUBLICATIONS

Willson, "Organic Resist Materials—Theory and Chemistry", [Introduction to Microlithography, Theory Materials, and Processing, Thompson et al., ACS Symp. Ser., Mar. 1983, vol. 219, pp. 87–159].

Primary Examiner—Marion E. McCamish
Assistant Examiner—Mark A. Chapman
Attorney, Agent, or Firm—Foley & Lardner

[57] ABSTRACT

Disclosed are compounds of the formula I

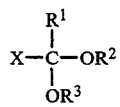

in which

X is a phenyl, [1]naphthyl or [2]naphthyl radical each substituted by at least one tert.-butoxycarbonyloxy group and, if appropriate, having one or more than one additional substituent, $R^1$ is a hydrogen atom, a ($C_1$–$C_6$)-alkyl radical, a ($C_6$–$C_{10}$)-aryl radical or one of the radicals X and $R^2$ and $R^3$ are identical or different and are a ($C_1$–$C_{12}$)-alkyl radical in which, if appropriate, up to three methylene groups are replaced by bridge members having at least one hetero atom, such as —O—, —S—, —NR$^4$—, —CO—, —CO—O—, —CO—NH—, —O—CO—NH—, —NH—CO—NH—, —CO—NH—CO—, —SO$_2$—, —SO$_2$—O— or —SO$_2$—NH—, a ($C_3$–$C_{12}$)-alkenyl, ($C_3$–$C_{12}$)-alkynyl, ($C_4$–$C_{12}$)-cycloalkyl, ($C_4$–$C_{12}$)-cycloalkenyl or ($C_8$–$C_{16}$)-aralkyl radical in which, if appropriate, up to three methylene groups of the aliphatic moiety are replaced by bridge members of the abovementioned type and which can be substituted in the aromatic moiety by fluorine, chlorine or bromine atoms or by ($C_1$–$C_4$)-alkyl, ($C_1$–$C_4$)-alkoxy, nitro, cyano or tert.-butoxycarbonyloxy groups, $R^4$ being an acyl radical, especially a ($C_1$–$C_6$)-alkanoyl radical.

17 Claims, No Drawings

COMPOUNDS WITH ACID-LABILE PROTECTIVE GROUPS USEFUL IN POSITIVE-WORKING RADIATION-SENSITIVE MIXTURES

BACKGROUND OF THE INVENTION

The present invention relates to compounds with acid-labile protective groups, to processes for the preparation of these compounds and to positive-working radiation-sensitive mixtures containing these compounds as solubility inhibitors. It also relates to a recording material prepared with these compounds, which is suitable for photoresists, electrical components and printing plates and also for chemical milling.

In the industrial manufacture of microelectronic components, a number of lithographic techniques are currently used, different demands being made in each case on the photoresist mixtures used therein. Thus, in g-line lithography, where radiation of a wavelength of 436 nm is employed, conventional diazonaphthoquinone/novolak photoresists are generally used. A more recent development is i-line lithography, in which radiation of a wavelength of 365 nm is used. Images with details of a mask original in improved resolution down to 0.5 $\mu$m can be obtained with this technique. More recent modifications, such as phase-shifting mask technology, permit a further reduction in image size down to about 0.35 $\mu$m and even finer. Even better resolution will become possible in the future by means of the "UV-2" photoresists. A distinction is here made between two variants: UV-2 wide-band irradiation (240 to 260 nm) and irradiation with KrF-excimer lasers (248 nm).

As can already be seen from the above, the limit of resolution is given by the wavelength of the radiation used. The continuing reduction in size of the structural dimensions, far down into the submicron region, especially for microchips, requires modified lithographic techniques. Because of their short wavelength, high-energy UV radiation, electron beams or X-rays are here particularly suitable, A review of the demands that are made on the radiation-sensitive mixtures used in a particular case, will be found in the article by C. G. Willson, "Organic Resist Materials-Theory and Chemistry" (Introduction to Microlithography, Theory, Materials and Processing; Editors: L. F. Thompson, C. G. Willson, M. J. Bowden; ACS Symp. Ser. 219: 87 (1983), American Chemical Society, Washington). There is therefore an increased demand for radiation-sensitive mixtures that can be used in the advanced technologies, especially in mid-UV lithography, deep-UV lithography, electron lithography and X-ray lithography. In addition, they are preferably sensitive within a wide spectral range and can thus also be used in conventional UV lithography.

A frequently used positive-working radiation-sensitive mixture for producing radiation-sensitive recording materials contains an o-quinonediazide derivative and a binder that is soluble in aqueous-alkaline solutions, for example, a novolak or a polyhydroxystyrene. However, the sensitivity of the recording materials to UV radiation, in particular high-energy short-wave radiation, for example, to the light of a KrF-excimer laser having a wavelength of 248 nm, or to electron beams is generally insufficient.

Positive-working radiation-sensitive mixtures in which a photoinitiator generates an acid as a result of the action of actinic radiation show an improved sensitivity. In a subsequent reaction, this acid cleaves an acid-cleavable material and thereby renders it soluble in aqueous-alkaline developers.

It is also known that compounds having phenolic OH groups can be "masked" by tert.-butoxycarbonyl groups. Acids cleave this derivative into the phenolic starting compound, carbon dioxide and isobutene. Such compounds can also be utilized as light-sensitive solubility inhibitors.

Radiation-sensitive mixtures with acid-cleavable solubility inhibitors always require a small quantity of a compound that, on irradiation, generates an acid that in turn effects the cleavage of the above-mentioned materials. As photolytic acid generators, onium salts, such as diazonium, phosphonium, sulfonium and iodonium salts of non-nucleophilic acids, such as $HSbF_6$, $HAsF_6$ or $HPF_6$, have especially been used. In addition, halogen compounds, especially trichloromethyltriazine derivatives or trichloromethyloxadiazole derivatives, o-quinonediazidesulfochlorides, o-quinonediazide-4-sulfonic acid esters, organometal/organohalogen combinations, bis(sulfonyl)diazomethanes, sulfonylcarbonyldiazomethanes or nitrobenzyl tosylates have been recommended.

Such mixtures, some of which have high sensitivities to actinic radiation, are called photocatalytic 3-component systems, since they contain, as essential constituents, a polymeric binder soluble in aqueous-alkaline solutions (in most cases a phenolic resin), a photoactive compound and an acid-cleavable solubility inhibitor. Among these mixtures, those have gained particular acceptance in practice which contain compounds with acetal groups as the acid-labile component, since these combine adequate cleavability on the one hand with adequate storage stability on the other hand, especially in the dissolved form. The acetal must here have, inter alia, a largely hydrophobic molecular backbone, in order to be able to function as a solubility inhibitor. Acetals having free phenolic hydroxyl groups are completely unsuitable as solubility inhibitors, since they enhance the solubility in aqueous-alkaline solutions.

Furthermore, it can be observed generally that the process window, i.e., the spectral range of transmission for the exposure of these mixtures, is very narrow and frequently not unambiguously reproducible, causing inaccurate reproductions of the original. The inadequately narrow process window manifests itself especially in a steep dependency of the quality of image reproduction on the time difference between exposure and development, the so-called delay time. The causes of this deterioration in the image reproduction are not known in detail or have not been adequately investigated. In principle, it must be assumed that diffusion processes, which cause this behavior, cannot readily be controlled. However, it maybe supposed that, during the drying of the mixture on a substrate material, a partial vaporization of the photoinitiator or of the acid-labile compound or a segregation of the individual mixture constituents takes place. This is particularly frequently observed in the case of acid-labile compounds having a low solubility in the usual coating solvents.

The decisive disadvantage of the known compounds containing acetal groups is the fact that the solubility differentiation between exposed and unexposed image areas resulting from the cleavage of these compounds, is generally insufficient. It appears that either the acetal derivative used as the solubility inhibitor has an inadequate inhibiting property and, in addition to the exposed image areas, those which have not been exposed are also severely attacked and worn off during imagewise differentiation, or that the exposed areas do not have an adequate solubility to allow imagewise differentiation during development. The problem is that the known compounds are unable to provide a material that causes a sufficiently large solubility difference between exposed and unexposed areas. Whereas this effect is still generally acceptable in the case of the novolak resins used according to the state of the art, it is observed, when other polymers are used, that the known acetal derivatives virtually cease to show any inhibiting action and therefore no longer allow an image differentiation as required in practice.

In the acid-catalyzed cleavage of 1 mol of the acetal, 1 mol of the corresponding aldehyde and 2 mol of alcohol are formed. In general, the alcohol contributes to the improved solubility in alkaline developers. By contrast, the aldehyde reduces the solubility, so that it is frequently evaporated out of the mixture by means of an additional baking step. It is more advantageous, however, to leave the aldehyde in the layer composed of the mixture, since it can be evaporated only in an uncontrollable manner, especially in the case of different layer thicknesses. This leads to non-reproducible results with respect to sensitivity and development behavior.

In both cases, best results ape therefore not obtained. If the solubility-inhibiting aldehyde generated by cleavage has to be evaporated out of the mixture, an additional processing step is necessary in order to obtain the best possible solubility of the exposed areas. If the aldehyde having an inhibiting action remains in the mixture, a differentiation of the solubility between exposed and unexposed layer areas, as required in practice, is not achieved. This has in turn particularly disadvantageous consequences if the mixture is used in a recording material. In this case, longer exposure and development times must be accepted, and the resulting relief image has, due to the inadequate solubility differentiation between exposed and unexposed areas, weaknesses in contrast, in the structural profile and in the wearing-off in the dark.

SUMMARY OF THE INVENTION

It is therefore an object of the present invention to provide compounds that effectively reduce the solubility in water, that have cleavage products that are very readily soluble in aqueous-alkaline developers, assisting the developing process in the exposed areas, and that have a low volatility, so that they do not evaporate out of the mixture even during a thermal aftertreatment, so that the properties of the radiation-sensitive mixture remain controllable.

These and other objects according to the invention are achieved by a compound of the formula I

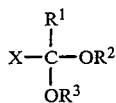

in which

X is a phenyl, [1]naphthyl or [2]naphthyl radical that is substituted by at least one tert.-butoxycarbonyloxy group and optionally by further substituents, $R^1$ is a hydrogen atom, a $(C_1-C_6)$-alkyl radical, a $(C_6-C_{10})$-aryl radical or one of the radicals X and $R^2$ and $R^3$ are identical or different and are a $(C_1-C_{12})$-alkyl radical in which up to three methylene groups are optionally replaced by bridge members having at least one hetero atom, said bridge members being selected from the group consisting of —O—, —S—, —NR$^4$—, —CO—, —CO—O—, —CO—NH—, —O—CO—NH—, —NH—CO—NH—, —CO—NH—CO—, —SO$_2$—, —SO$_2$—O— or —SO$_2$—NH—, a $(C_3-C_{12})$-alkenyl, $(C_3-C_{12})$-alkynyl, $(C_4-C_{12})$-cycloalkyl, $(C_4-C_{12})$-cycloalkenyl or $(C_8-C_{16})$-aralkyl radical, up to three methylene groups of the aliphatic moiety of the $(C_8-C_{16})$-aralkyl radical being optionally replaced by bridge members of the abovementioned type and the aromatic moiety of the $(C_8-C_{16})$-aralkyl radical being optionally substituted by fluorine, chlorine or bromine atoms or by $(C_1-C_4)$-alkyl, $(C_1-C_4)$-alkoxy, nitro, cyano or tert.-butoxycarbonyloxy groups, $R^4$ being an acyl radical.

Also provided according to the present invention is a process for preparing a compound according to formula I, comprising the steps of converting, in a first stage, an aldehyde or ketone of the formula II

by means of a low-boiling alcohol in the presence of a catalyst and of a dehydrating agent into an acetal or ketal of the formula III

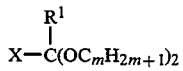

and then converting the acetal or ketal of formula III, in a second stage, by reaction with a high-boiling alcohol $R^2$—OH and/or $R^3$—OH in the presence of a catalyst into the compound of the formula I.

A positive-working radiation-sensitive mixture according to the invention comprises (a) a compound that generates a strong acid under the action of actinic radiation, (b) a compound according Go formula I having at least one C—O—C bond that can be cleaved by the acid generated by the compound (a), and (c) a binder that is insoluble in water but soluble or at least swellable in aqueous-alkaline solution. A radiation-sensitive recording material according to the invention comprises a layer of this mixture containing the compound according to formula I that is coated on a substrate.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Novel substituted acetals and ketals are provided according to the invention that are cleaved under the action of a sufficiently strong acid and thereby release a hydroxy-substituted aromatic aldehyde or a hydroxy-substituted aromatic ketone. The novel compounds are represented by the formula I

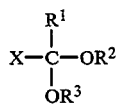

in which
- X is a phenyl, [1]naphthyl or [2]naphthyl radical each substituted by at least one tert.-butoxycarbonyloxy group and, if appropriate, having one or more than one additional substituent,
- $R^1$ is a hydrogen atom, a $(C_1-C_6)$-alkyl radical, a $(C_6-C_{10})$-aryl radical or one of the radicals X, and
- $R^2$ and $R^3$ are identical or different and are a $(C_1-C_{12})$-alkyl radical in which, if appropriate, up to three methylene groups are replaced by bridge members having at least one hetero atom, such as —O—, —S—, —$NR^4$—, —CO—, —CO—O—, —CO—NH—, —O—CO—NH—, —NH—CO—NH—, —CO—NH—CO—, —$SO_2$—, —$SO_2$—O— or —$SO_2$—NH—, a $(C_3-C_{12})$-alkenyl, $(C_3-C_{12})$-alkynyl, $(C_4-C_{12})$-cycloalkyl, $(C_4-C_{12})$-cycloalkenyl or $(C_8-C_{16})$-aralkyl radical in which, if appropriate, up to three methylene groups of the aliphatic moiety are replaced by bridge members of the abovementioned type and which can be substituted in the aromatic moiety by fluorine, chlorine or bromine atoms or by $(C_1-C_4)$-alkyl, $(C_1-C_4)$-alkoxy, nitro, cyano or tert.-butoxycarbonyloxy groups,
- $R^4$ being an acyl radical, especially a $(C_1-C_6)$-alkanoyl radical.

The substituents that may additionally be present in the radicals X are preferably fluorine, chlorine, bromine or iodine atoms, nitro, cyano or carboxyl groups, $(C_1-C_9)$- and particularly preferably $(C_1-C_6)$-alkyl radicals in which, if appropriate, up to three and particularly preferably up to two methylene groups are replaced by bridge members of the abovementioned type, phenyl radicals which may in turn be substituted, especially by tert.-butoxycarbonyl groups, $(C_1-C_4)$-alkyl radicals, $(C_1-C_4)$-alkoxy radicals and/or halogen atoms, and also $(C_8-C_{12})$- and particularly preferably $(C_8-C_{10})$-aralkyl radicals in which, if appropriate, up to two methylene groups are replaced by bridge members of the abovementioned type, $(C_6-C_{10})$-aryloxy radicals or $(C_7-C_{10})$-aralkoxy radicals.

The bridge members containing hetero atoms in the alkyl and aralkyl radicals can be present within the alkyl chain or represent the member linked to the radical X.

Compounds of the formula I in which X is a substituted phenyl radical are generally preferred. Compounds of the formula I in which $R^1$, furthermore, is a hydrogen atom are particularly preferred.

The compounds according to the invention represent acetals or ketals that have a pronounced hydrophobic character and are therefore suitable as solubility inhibitors, whereas the products resulting from the acid-catalyzed cleavage of these compounds are extraordinarily hydrophilic and therefore act as solubility enhancers.

The invention also relates to a process for preparing the compounds of the formula I, wherein a carbonyl compound of the formula II

in which X and $R^1$ have the definitions given above, is reacted with a low-boiling alcohol in the presence of a catalyst to give the corresponding acetal or ketal of the formula III

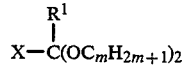

The low-boiling alcohol is preferably methanol or ethanol, i.e. m is preferably 1 or 2.

In order irreversibly to remove the water of reaction that is formed during the reaction, the mixture advantageously contains a suitable dehydrating agent, for example, a drying agent.

The compounds according to the invention of the formula I are then obtained by reaction with higher-boiling alcohols $R^2$—OH and/or $R^3$—OH in the presence of a catalyst.

The compounds of the formula II can be prepared from the corresponding aromatic aldehydes or ketones substituted by hydroxy groups in a manner known per se (F. Houlihan et al., Can. J. Chem., 63: 153 (1985)) by reaction with tert.-butoxycarbonyl chloride or di-tert.-butyl pyrocarbonate.

Particularly preferred starting materials are hydroxy-substituted aromatic aldehydes such as 2-, 3- and 4-hydroxybenzaldehyde, 2,3-, 2,4-, 2,5- and 3,4-dihydroxybenzaldehyde, 2,3,4-trihydroxybenzaldehyde, 4-hydroxy-3-methylbenzaldehyde, 2-hydroxy-4- and -5-methoxybenzaldehyde, 3-hydroxy-4-methoxybenzaldehyde, 4-hydroxy-3-methoxybenzaldehyde, 3,5-dimethyl-4-hydroxybenzaldehyde, 3,4-dimethoxy-5-hydroxybenzaldehyde, 3-ethoxy-4-hydroxybenzaldehyde, 2-hydroxy-5-nitrobenzaldehyde, 3-hydroxy-4-nitrobenzaldehyde, 4-hydroxy-3-nitrobenzaldehyde, 5-hydroxy-2-nitrobenzaldehyde or 2-hydroxy-1-naphthaldehyde.

These aldehydes are commercially available, whereas other aromatic hydroxy-aldehydes or -ketones likewise suitable as precursors can in general be prepared in a simple manner by the most diverse methods (see Houben Weyl, METHODEN DER ORGANISCHEN CHEMIE [METHODS OF ORGANIC CHEMISTRY], volume 7/1).

To avoid cleavage of the tert.-butoxycarbonyloxy group, the acetalization or ketalization of the compounds of the formula II is carried out with the low-boiling alcohols in the presence of a special catalyst. Catalysts of the type of the rhodium phosphine complexes have proven suitable. Catalysts of the $RhCl_3$ (triphos) type are preferred. Particularly preferred is the catalyst $RhCl_3[CH_3C(CH_2PPh_2)_3]$.

The required quantity of the catalyst is generally between about 0.1 mg and 10 mg per 1 mmol of aldehyde, and preferably between about 0.5 and 1 mg of catalyst per 1 mmol of aldehyde. These catalysts have been described by J. Ott et al. in J. Organomet. Chem., 291: 89 (1985) and Tetrahedr. Lett., 30: 6151 (1989).

The acetalization or ketalization is advantageously carried out at temperatures between about 0° C. and 100° C. Temperatures between about 10° C. and 50° C., especially room temperature, are preferred. The reaction time is between about 20 minutes and 48 hours, especially between about 4 and 16 hours.

The reaction can be carried out in the presence of a solvent that is inert under the reaction conditions. Aromatic hydrocarbons such as toluene and xylene are particularly suitable. The solvent is added in a 0.5 to 50-fold excess.

For irreversible removal of the water of reaction formed, the trialkyl orthoformate corresponding to the alcohol, preferably trimethyl or triethyl orthoformate, is added to the reaction mixture.

The mixture is worked up by known methods. Yields of more than 90% are obtained.

The acetalization or ketalization of the compounds of the formula II can also be carried out in the presence of other neutral or very weakly acidic catalysts, such as acidic exchanger resins or organic acids. However, these catalysts lead to an incomplete conversion or to transesterification and hence to difficulties in working-up and to a reduction in the product yield and purity.

With the abovementioned rhodium catalysts, the aldehydes or ketones of the formula II can also be reacted directly with the higher-boiling alcohols $R^2$—OH and/or $R^3$—OH. However, this raises problems in working-up, which do not arise in the two-stage process described above.

The compounds according to the invention of the formula I are then obtained from the compounds of the formula III in a second stage by reaction with a stoichiometric quantity of high-boiling alcohols $R^2$—OH and/or $R^3$—OH in an inert solvent, such as toluene or xylene, in the presence of an acidic catalyst. Here again, in order to avoid decomposition of the tert.-butoxycarbonyloxy group, only weakly acidic catalysts insoluble in the reaction mixture are used. Potassium hydrogen sulfate or an acidic ion exchanger resin are preferably used as catalyst.

For each mmol of acetal or ketal employed, 1 to 100 mg of catalyst are used. The preferred quantity ratio is 5 to 10 mg of catalyst/mmol of carbonyl derivative. To increase the reaction rate, the reaction is carried out at temperatures of more than about 75° C., and temperatures between about 100° and 150° C. are preferred.

The compounds of the formula I are obtained from the compounds of the formula III in a yield of 75 to 98% of that theoretically possible.

The compounds according to the invention of the formula I are outstandingly suitable for the preparation of positive-working radiation-sensitive mixtures which can be used in radiation-sensitive layers for photo-resists or printing plates.

The present invention further relates to a positive-working radiation-sensitive mixture with
  (a) a compound that generates a strong acid under the action of actinic radiation,
  (b) a compound having at least one C—O—C bond that can be cleaved by the acid generated by the compound (a), and
  (c) a binder that is insoluble in water but soluble or at least swellable in aqueous-alkaline solution,
wherein the compound (b) is a compound of the formula I.

The radiation-sensitive mixture according to the invention is distinguished by high sensitivity and a wide spectral range. It shows high thermal stability and allows even superfine structures of an original to be reproduced in true detail.

The content of acid-cleavable material (b) in the radiation-sensitive mixture according to the invention should be about 1 to 60% by weight and preferably about 5 to 50% by weight, each relative to the total weight of the solid constituents of the mixture.

If desired, the mixtures according to the invention can also contain other acid-cleavable compounds. Above all the following classes of compounds have proven suitable for this purpose:
1. those having at least one orthocarboxylate and/or orthocarboxamide-acetal grouping, it also being possible for the compounds to have a polymeric character and for the said groupings to appear as linking elements in the main chain or as side-chain substituents (DE 2,610,842 and 2,928,636),
2. oligomeric or polymeric compounds having recurring acetal and/or ketal groupings in the main chain (DE 2,306,248 and 2,718,254),
3. compounds having at least one enol ether or N-acyliminocarbonate grouping (EP 0,006,626 and 0,006,627),
4. cyclic acetals or ketals of β-keto-esters or -amides (EP 0,202,196),
5. compounds having silyl ether groupings (DE 3,544,165 and 3,601,264),
6. compounds having silyl enol ether groupings (DE 3,730,785 and 3,730,783),
7. monoacetals or monoketals whose aldehyde or ketone component has a solubility in the developer between 0.1 and 100 g/l (DE 3,730,787),
8. ethers based on tertiary alcohols (U.S. Pat. No. 4,603,101) and
9. carboxylates and carbonates of tertiary, allylic or benzylic alcohols [U.S. Pat. No. 4,491,628 and J. M. Frechet et al., *J. Imaging Sci.* 30: 59–64 (3986)].

These materials can also be present as mixtures. In this case, it is preferred that the acid-cleavable materials correspond to only one of the abovementioned types, including here with particular preference those having at least one acid-cleavable C—O—C bond, i.e., those belonging to types (1), (2), (7) and (9). Under type (2), the polymeric acetals and, from the acid-cleavable materials of type (7), especially those derived from aldehydes or ketones having a boiling point above about 150° C., preferably above about 200° C., are to be singled out.

To the acid-cleavable compounds (b) contained in the radiation-sensitive mixture according to the invention, photolytic acid generators (a) are added, for which purpose onium salts, such as diazonium, phosphonium, sulfonium and iodonium salts of non-nucleophilic acids, for example, of $HSbF_6$, $HAsF_6$ or $HPF_6$ [J. V. Crivello, *Polym. Eng. Sci.*, 23: 953 (1983)] are suitable only with restrictions, since highly corrosive acids can be generated. Photolytic acid generators that generate sulfonic acids on exposure are preferred. Examples of such compounds include 1,2-disulfones, bis-sulfonyl-diazomethane (DE 3,930,086) and sulfonyl-carbonyl-diazomethane (DE 3,930,087), nitrobenzyl sulfonates (F. M. Houlihan et al., *J. Photopolym. Sci. Techn.*, 3: 259, (1990); T. Yamaoka et al., *J. Photopolym. Sci. Techn.*, 3: 275, (1990)), pyrogallol sulfonates (L. Schlegel et al., *J. Photopolym. Sci. Techn.*, 3: 281, (1990)) or iminosulfonates (M. Shirai et al., *J. Photopolym. Sci. Techn.*, 3: 301 (1990)). Onium salts that generate perfluorosulfonic acids and the 1-sulfonyloxy-2-pyridones mentioned in German Patent Application P 4,112,967.9 are particularly preferred.

The photolytic acid generators are added to the mixture in a proportion of about 0.2 to 25% by weight. Proportions of about 0.5 to 15% by weight are preferred, and about 1 to 10% by weight, relative to the total weight of the solid constituents of the mixture, are particularly preferred, the nature of the components (a) to (c) determining the mutual ratio of the compounds used.

The photolytic acid generators have absorption maxima in the range between 200 and 500 nm. They fix the spectral sensitivity of the mixtures according to the invention. They can be selected in such a way that sensitivities as required in practice in the region of the technically important radiation sources, e.g., g-line (436 nm), i-line (365 nm) or UV-2 (248 nm), can be achieved. The acid-cleavable compounds (b) that can be used according to the invention can here be selected such that they have virtually no characteristic absorption in these regions. By means of spectral sensitization, the sensitivity range of the acid-generating compounds (a) can be widened to such an extent that radiation sources of the visible region or shortwave X-ray region can also be used. Finally, other radiation sources, such as electron beams or ion beams, can also be used for the imagewise differentiation of the mixture according to the invention, especially if highly active acid generators (EP 0,318,649) are employed.

The radiation-sensitive mixture according to the invention also contains at least one polymeric binder (c) that is insoluble in water but soluble or at least swellable in aqueous-alkaline solutions. The selection of the suitable binder depends largely on the type of use. The binder is especially distinguished by the fact that it readily dissolves the constituents of the radiation-sensitive mixture according to the invention, permits aqueous-alkaline developability and especially has the lowest possible characteristic absorption, i.e., high transparency, especially in the wavelength range of the incident radiation from 190 to 550 nm.

For the conventional applications i.e., using light sources in the near-UV region, binders based on novolak condensation resins, that have generally been used in combination with naphthoquinonediazides as photoactive components, are particularly suitable for this purpose. Such phenol/formaldehyde condensates have been described many times and can contain, as the phenolic component, phenol, the three positionally isomeric cresols or other alkylphenols, e.g., xylenols, as components. In addition to formaldehyde, other aldehydes car also be utilized for preparing the polymer. The polymers containing hydroxyl groups, that are described below, can equally well be used for irradiations with near-UV light.

Other polymeric materials are, however, necessary for applications in the UV-2 region. Novolaks that as a rule are used in combination with naphthoquinonediazides as photoactive components are unsuitable for this purpose. They can, however, be used as a mixture with other resins suitable as binders and having a higher transparency. The mixing ratios then depend predominantly on the nature of the binder to be mixed with the novolak resin. In particular, the degree of characteristic absorption thereof in the specified wavelength region and also the miscibility with the other constituents of the radiation-sensitive mixture then play a decisive part. In general, however, the binder of the radiation-sensitive mixture according to the invention can contain up to about 50% by weight and especially up to about 20% by weight of a novolak condensation resin.

Suitable binders are homopolymers or copolymers of p-hydroxystyrene and of its alkyl derivatives, for example, of 3-methyl-4-hydroxystyrene, of 3,5-dimethyl-4-hydroxystyrene or of 2,3-dimethyl-4-hydroxystyrene, and homopolymers or copolymers of other polyvinylphenols, for example, of 3-hydroxystyrene, or of 4-methyl-3-hydroxystyrene or the esters of (meth)acrylic acid with phenols, for example, pyrocatechol, resorcinol, hydroquinone or pyrogallol, or aminophenols, and the corresponding amides with aromatic amines. The comonomers used can be polymerizable compounds such as styrene, methyl methacrylate, methyl acrylate or the like.

Mixtures of enhanced plasma resistance are obtained if silicon-containing vinyl monomers, for example, vinyl trimethylsilane or allyltrimethylsilane, are used for the preparation of copolymers of the above type. The transparency of these binders in the region of interest is generally higher, so that improved is possible.

Homopolymers or copolymers of maleimide can also be used equally well. These binders again show high transparency in the wavelength region described. Here again, the comonomers used are preferably styrene, substituted styrenes, vinylphenols, vinyl ethers, vinyl esters, vinylsilyl compounds or (meth)acrylates.

Finally, copolymers of styrene with comonomers that effect an increase in the solubility in aqueous-alkaline solutions can also be used. These include, for example, maleic anhydride and maleic acid half-esters.

The binders can be mixed with one another if the optical quality of the radiation-sensitive mixture is not adversely affected thereby. However, binder mixtures are not preferred.

The quantity of the binder is generally about 30 to 95% by weight, especially about 40 to 90% by weight and preferably about 50 to 85% by weight, relative to the total weight of the solid constituents of the radiation-sensitive mixture.

The extinction of the binder or of the combination of binders for radiation of the wavelength from about 220 to 500 nm should be less than about 0.5, preferably less than about 0.3 $\mu m^{-1}$.

If appropriate, dyes, pigments, plasticizers, wetting agents and leveling agents, and also polyglycols, cellulose ethers, e.g., ethylcellulose, can also be added to the radiation-sensitive mixtures according to the invention in order to meet special requirements, such as flexibility, adhesion and gloss.

If a substrate is to be coated, the radiation-sensitive mixture according to the invention is appropriately dissolved in a solvent or in a combination of solvents. Particularly suitable for this purpose are ethylene glycol and propylene glycol and the monoalkyl and dialkyl ethers derived therefrom, especially the monomethyl and dimethyl ethers and the monoethyl and diethyl ethers, esters derived from aliphatic ($C_1$–$C_6$)-carboxylic acids and either ($C_1$–$C_8$)-alkanols or ($C_1$–$C_8$)-alkanediols or ($C_1$–$C_6$)-alkoxy-($C_1$–$C_8$)-alkanols, for example, ethyl acetate, hydroxyethyl acetate, alkoxyethyl acetate, n-butyl acetate, propylene glycol monoalkyl ether-acetate, especially propylene glycol methyl ether-acetate, and amyl acetate, ethers such as tetrahydrofuran and dioxane, ketones such as methyl ethyl ketone, methyl isobutyl ketone, cyclopentanone and cyclohexanone, N,N-dialkyl-carboxamides such as N,N-dimethylformamide and N,N-dimethylacetamide, and also hexamethylphosphotriamide, 1-methyl-pyrrolidin-2-one and butyrolactone, as well as any desired mixtures thereof. Among these, the glycol ethers, aliphatic esters and ketones are particularly preferred.

Ultimately, the selection of the Solvent or solvent mixture depends on the coating process used, on the desired layer thickness and on the drying conditions. In addition, the solvents must be chemically neutral, i.e., they must not irreversibly react with the other layer components.

The solution prepared with the Solvents generally has a solids content of about 5 to 60% by weight, preferably up to about 50% by weight.

Finally, the invention also relates to a radiation-sensitive recording material comprising a substrate with a radiation-sensitive layer composed of the radiation-sensitive mixture according to the invention.

The substrates can be all those materials of which capacitors, semiconductors, multi-layer printed circuits or integrated circuits are composed or from which these can be prepared. Silicon substrates, that optionally have been thermally oxidized and/or coated with aluminum or doped, deserve special mention. In addition, all other substrates conventional in semiconductor technology are possible, such as silicon nitride, gallium arsenide and indium phosphide. The substrates known from liquid crystal display production can also be used, such as glass or indium/tin oxide, and also metal plates and foils, for example, of aluminum, copper and zinc, bimetal foils and trimetal foils, and also electrically non-conductive foils on which metals have been vapor-deposited, and paper. These substrates can have been thermally pretreated, superficially roughened, incipiently etched or pretreated with chemicals to improve desired properties, for example, to enhance the hydrophilic character.

In order to provide the radiation-sensitive layer with better cohesion and/or better adhesion to the substrate surface, it can contain an adhesion promoter. The same effect can be achieved by an adhesion-promoting interlayer. In the case of silicon substrates and silica substrates, adhesion promoters of the aminosilane type, such as, for example, 3-aminopropyltriethoxysilane or hexamethyldisilazane, can be used for this purpose.

Suitable supports for the production of photomechanical recording layers, such as printing forms for letterpress printing, planographic printing, screen printing and flexographic printing, are especially aluminum plates that may be anodically oxidized, grained and/or silicatized beforehand, and also zinc plates and steel plates that may be chromium-plated, and also plastic films and paper.

The recording material according to the invention is exposed imagewise to actinic radiation. Suitable radiation sources are especially metal halide lamps, carbon arc lamps, xenon lamps and mercury vapor lamps. Exposure can also be carried out with high-energy radiation such as laser radiation, electron beams or X-rays. However, lamps that can emit light of a wavelength from 190 to 260 nm, i.e., especially xenon lamps and mercury vapor lamps, are particularly preferred. Furthermore, laser light sources can also be used, e.g., excimer lasers, especially KrF or ArF lasers, that emit at 248 or 193 nm, respectively. The radiation sources must show an adequate emission within the wavelength ranges.

Within the scope of this description, actinic radiation is to be understood as any radiation whose energy corresponds at least to that of shortwave visible light. Longwave and shorter-wave UV radiation such as is emitted, for example, by excimer lasers, is therefore particularly suitable.

The thickness of the light-sensitive layer depends on the intended use. It is generally between about 0.1 and 100 $\mu$m, preferably between about 1 and 10 $\mu$m.

The invention further relates to a process for producing a radiation-sensitive recording material. The application of the radiation-sensitive mixture to the substrate can be effected by spraying, flow-coating, roller application, whirler-coating and dip-coating. Subsequently, the solvent is removed by evaporation, so that the radiation-sensitive layer remains on the surface of the substrate. The removal of the solvent can be promoted by heating the layer to temperatures of up to about 150° C. The mixture can, however, also be applied first in the abovementioned Way to a temporary support, from which it is transferred under pressure and at an elevated temperature to the final support material. The temporary supports used can in principle be any material that is suitable as support material. Subsequently, the layer is irradiated imagewise. It is then treated with a developer solution that dissolves and removes the irradiated areas of the layer, so that an image of the original used in the imagewise irradiation remains on the substrate surface.

Suitable developers are especially aqueous solutions that contain silicates, metasilicates, hydroxides, hydrogen phosphates and dihydrogen phosphates, carbonates or hydrogen carbonates of alkali metal ions, alkaline earth metal ions and/or ammonium ions, and also ammonia and the like. Metal ion-free developers are described in U.S. Pat. No. 4,729,941, EP 0,062,733, U.S. Pat. No. 4,628,023, U.S. Pat, No. 4,141,733, EP 0,097,282 and EP 0,023,758. The content of these substances in the developer solution is generally about 0.1 to 15% by weight, preferably about 0.5 to 5% by weight, relative to the weight of the developer solution. Metal ion-free developers are preferably used. Small quantities of a wetting agent can have been added to the developers in order to facilitate the detachment of the soluble areas of the layer.

The developed layer structures can be posthardened. This generally is effected by heating on a hotplate up to a temperature below the flow temperature and subsequent whole-area exposure to the UV light of a xenon/mercury vapor lamp (range from 200 to 250 nm). The image structures are crosslinked by the posthardening, so that they generally have a flow resistance up to temperatures of more than 200° C. The posthardening can also be effected without an increase in temperature, solely by irradiation with high-energy UV light in a high dosage.

The radiation-sensitive mixture according to the invention is used in the manufacture of integrated circuits or of individual electrical components by lithographic processes, since they have a high light sensitivity, particularly when irradiated with light of a wavelength between about 190 and 300 nm. Since the mixtures bleach very well on exposure, finer structures can be achieved than is possible with the known mixtures. The developed resist layer here serves as a mask for the subsequent process steps. Examples of such steps are the etching of the layer support, the implantation of ions into the layer support or the deposition of metals or other materials on the layer support.

The examples described below illustrate the invention, but they are not intended to effect any restriction. Percentage data are always percent by weight, and melting points are uncorrected unless otherwise stated. P.b.w. means parts by weight below.

EXAMPLE 1

1st stage: Preparation of 4-tert.-butoxycarbonyloxy-benzaldehyde dimethylacetal Two g (9 mmol) of 4-(tert.-butoxycarbonyloxy)-benzaldehyde were dissolved at room temperature in 10 ml of methanol and 1.2 ml of trimethyl orthoformate. To obtain complete solution, 1.5 ml of toluene were added. This was followed by the addition of 3.75 mg of $RhCl_3[CH_3C(CH_2PPh_2)_3]$ as catalyst. The mixture was then stirred overnight at room temperature. The solvents were separated off by steam distillation and the oily residue was taken up in a little toluene. The rhodium catalyst was filtered off over a G-4 frit. After the toluene had been stripped off under reduced pressure, the product was dried in an oil pump vacuum.

Yield 2.3 g (95% of theory), pale yellow oil, H-NMR ($CDCl_3$): acetal signal at 5.38 ppm, BOC signal at 1.56 ppm, CO signal in the IR spectrum at 1760 cm$^{-1}$ (compound 1).

2nd stage: Preparation of 4-tert.-butoxycarbonyloxy-benzaldehyde bis-(2-phenoxyethyl)-acetal A mixture of 2 g (7.45 mmol) of 4-(tert.-butoxycarbonyloxy)-benzaldehyde dimethylacetal, 2.06 g (14.9 mmol) of 2-phenoxyethanol and 40 mg of potassium hydrogensulfate was heated to the boil in 30 ml of dried toluene under a reflux condenser. After heating for 1 hour, the methanol formed was distilled off slowly, while more toluene was added to the mixture. After complete removal of the methanol, the mixture was cooled down, the potassium hydrogen sulfate catalyst was filtered off and the toluene was stripped off. The oily residue was dissolved in dichloromethane and washed with water. The organic phase was dried over magnesium sulfate. After the solvent had been stripped off under reduced pressure, the product was dried in an oil pump vacuum.

Yield 3.26 g (91% of theory), pale yellow oil which has crystallized out after 2 days (melting point 39 to 40° C.). H-NMR ($CDCl_3$): acetal signal at 5.77 ppm, BOC signal at 1.57 ppm, CO signal in the IR spectrum at 1760 cm$^{-1}$. The mass spectrum shows a molar mass of M=480 (compound 2).

EXAMPLE 2

1st stage: Preparation of 3-tert.-butoxycarbonyloxy-benzaldehyde dimethylacetal Two g (9 mmol) of 3-tert.-butoxycarbonyloxy-benzaldehyde were dissolved at room temperature in 10 ml of methanol and 1.2 ml of trimethyl orthoformate. To obtain complete solution, 1.5 ml of toluene were added. This was followed by the addition of 3.75 mg of $RhCl_3[CH_3C(CH_2PPh_2)_3]$ as catalyst. The mixture was then stirred overnight at room temperature. The solvents were separated off by steam distillation, and the oily residue was taken up in a little toluene. The rhodium catalyst was filtered off over a G-4 frit. After the toluene had been stripped off under reduced pressure, the product was dried in an oil pump vacuum.

Yield 2.1 g (85% of theory), pale yellow oil, H-NMR ($CDCl_3$): acetal signal at 5.35 ppm, BOC signal at 1.55 ppm, CO signal in the IR spectrum at 1760 cm$^{-1}$ (compound 3).

2nd stage: Preparation of 3-tert.-butoxycarbonyloxy-benzaldehyde bis-(2-phenylethyl)-acetal One g (3.73 mmol) of 3-tert.-butoxycarbonyloxy-benzaldehyde dimethylacetal was dissolved in 40 ml of dried toluene. After addition of 0.91 g (7.46 mmol) of 2-phenylethanol and 18 mg of potassium hydrogen sulfate, the resulting mixture was stirred for 2 hours under reflux. The methanol formed was then distilled off slowly, while more toluene was added to the mixture. After complete removal of the methanol, the mixture was cooled down and the potassium hydrogen sulfate was filtered off. The filtrate was concentrated in a rotary evaporator. This gave a yellowish, viscous oil, which was dried in an oil pump vacuum.

Yield 1.59 g (95% of theory). H-NMR ($CDCl_3$): acetal signal at 5.50 ppm, BOC signal at 1.57 ppm, CO signal in the IR spectrum at 1760 cm$^{-1}$ (compound 4).

EXAMPLE 3

1st stage: Preparation of 3-methoxy-4-tert.-butoxycarbonyloxy-benzaldehyde diethylacetal An amount of 1.52 g (6 mmol) of 3-methoxy-4-tert.-butoxycarbonyloxy-benzaldehyde was dissolved in 18 ml of ethanol and 2 ml of triethyl orthoformate. For complete solution of the 3-methoxy-4-tert.-butoxycarbonyloxy-benzaldehyde, a further 2 ml of toluene were added. This was followed by the addition of 4.2 mg of $RhCl_3[CH_3C(CH_2PPh_2)_3]$ as catalyst. The reaction solution was then stirred at room temperature until starting material was no longer detectable in the thin-layer chromatogram. After the solvents had been stripped off, the oily residue was dissolved in a little toluene and filtered over a G-4 frit. The resulting solution was concentrated in a rotary evaporator and dried in an oil pump vacuum.

Yield 1.72 g (88% of theory), pale yellow oil, H-NMR ($CDCl_3$): acetal signal at 5.44 ppm, BOC signal at 1.55 ppm, $CH_3O$ signal at 3.73 ppm, CO signal in the IR spectrum at 1760 cm$^{-1}$ (compound 5).

2nd stage: Preparation of 3-methoxy-4-tert.-butoxycarbonyloxy-benzaldehyde di-(phenylethyl)-acetal An amount of 1.1 g (3.36 mmol) of 3-methoxy-4-tert.-butoxycarbonyloxy-benzaldehyde diethylacetal was dissolved in 40 ml of dried toluene. After the addition of 0.82 g (6.71 mmol) of phenylethanol and 16 mg of potassium hydrogen sulfate, the resulting mixture was stirred for 2 hours under reflux. The ethanol formed was then distilled off slowly, while more toluene was added to the mixture. After complete removal of the ethanol, the mixture was cooled down and the potassium hydrogen sulfate was filtered off. The filtrate was concentrated in a rotary evaporator. This gave a yellowish, viscous oil, which was dried on an oil pump.

Yield 1.56 g (97% of theory), H-NMR ($CDCl_3$): acetal signal at 5.45 ppm, BOC signal at 1.55 ppm, CO signal in the IR spectrum at 1760 cm$^{-1}$ (compound 6).

EXAMPLE 4

1st stage: Preparation of 4-tert.-butoxycarbonyloxy-benzyl alcohol

Ten g (137.5 mmol) of $K_2CO_3$ were suspended in 150 ml of $CH_2Cl_2$, and 6.2 g (50 mmol) of 4-hydroxybenzyl alcohol were added. The alcohol did not completely dissolve. The reaction mixture was cooled to 0° C. At this temperature, 660 mg (2.5 mmol) of 18-crown-6-ether in 10.7 ml=10.9 g (50 mmol) of di-tert.-butyl dicarbonate were added dropwise. The mixture was stirred for some time at 0° C. and overnight at room temperature. The starting material was then no longer detectable, as shown by a thin-layer chromatogram ($SiO_2$, 1:1 petroleum ether: ethyl acetate). The potassium carbonate was then filtered off. The reaction mixture was diluted with methylene chloride, washed three times with saturated sodium chloride solution and then dried over magnesium sulfate. The magnesium sulfate was filtered off, and the filtrate was concentrated and then chromatographed over an $SiO_2$ column with 1:1 petroleum ether:ethyl acetate. This gave 8 g (71% of theory) of a colorless oil as product.

2nd stage: Preparation of
4-tert.-butoxycarbonyloxy-benzaldehyde
bis-(4-tert.-butoxycarbonyloxy-benzyl)acetal A mixture of 1 g (3.73 mmol) of 4-tert.-butoxycarbonyloxy-benzaldehyde dimethylacetal, prepared according to stage 1 of Example 1, 1.67 g (7.46 mmol) of 4-tert.-butoxycarbonyloxy-benzyl alcohol and 18 mg of potassium hydrogen sulfate was heated in 40 ml of dried toluene for 1 hour under reflux. The methanol formed was then slowly distilled off, with addition of toluene. After complete removal of the methanol, the mixture was cooled down, the catalyst was filtered off and the toluene was stripped out. The oily residue was dried in an oil pump vacuum.

Yield 2.33 g (96% of theory), pale yellow wax, H-NMR ($CDCl_3$): acetal signal at 5.71 ppm, BOC signal at 1.55 ppm, $CH_2O$ signal at 4.54 ppm, CO signal in the IR spectrum at 1760 $cm^{-1}$ (compound 7).

EXAMPLE 5

1st stage: Preparation of
2,3-bis-tert.-butoxycarbonyloxy-benzaldehyde
dimethylacetal Three g (9 mmol) of 2,3-bis-tert.-butoxycarbonyloxy-benzaldehyde were dissolved at room temperature in 10 ml of methanol and 1.2 ml of trimethyl orthoformate. For complete dissolution of the benzaldehyde derivative, 1.5 ml of toluene were added. This was followed by the addition of 3.75 mg of $RhCl_3[CH_3C(CH_2PPh_2)_3]$ as catalyst. The mixture was then stirred overnight at room temperature. The solvents were separated off by steam distillation and the oily residue was taken up in a little toluene. The undissolved rhodium catalyst was filtered off over a G-4 frit. After the toluene had been stripped off under reduced pressure, the product was dried in an oil pump vacuum.

Yield 2.9 g (75% of theory), pale yellow oil, H-NMR ($CDCl_3$): acetal signal at 5.30 ppm, BOC signal at 1.55 ppm, CO signal in the IR spectrum at 1760 $cm^{-1}$ (compound 8).

2nd stage: Preparation of
2,3-bis-tert.-butoxycarbonyloxy-benzaldehyde
bis-(2-phenylethyl)-acetal An amount of 1.43 g (3.73 mmol) of 2,3-bis-tert.-butoxycarbonyloxy-benzaldehyde dimethylacetal was dissolved in 40 ml of dried toluene. After the addition of 0.91 g (7.46 mmol) of 2-phenylethanol and 18 mg of potassium hydrogen sulfate, the resulting mixture was stirred for 1 hour under reflux. The methanol formed was then distilled off slowly, while more toluene was added to the mixture. After complete removal of the methanol, the mixture was cooled down and the potassium hydrogensulfate was filtered off. The filtrate was concentrated in a rotary evaporator. This gave a yellowish, viscous oil which was dried in an oil pump vacuum.

Yield 1.66 g (79% of theory), H-NMR ($CDCl_3$): acetal signal at 5.48 ppm, BOC signal at 1.54 ppm, CO signal in the IR spectrum at 1760 $cm^{-1}$ (compound 9).

The structural formulae of compounds 1 to 9 are shown below.

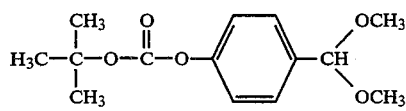

Compound No. 1

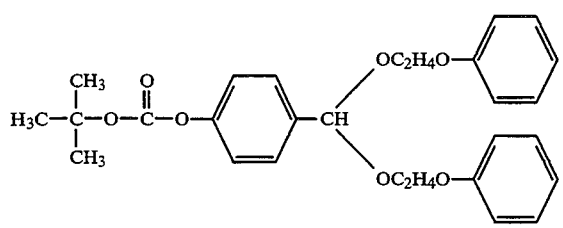

Compound No. 2

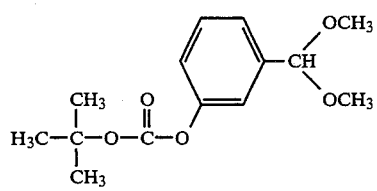

Compound No. 3

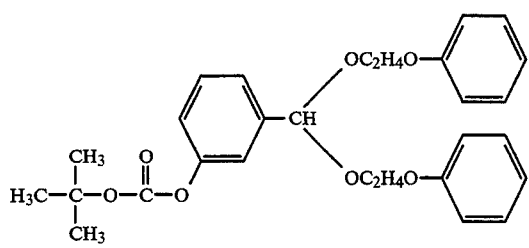

Compound No. 4

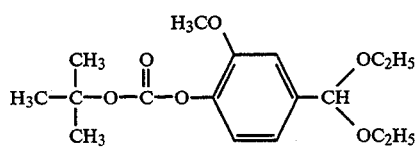

Compound No. 5

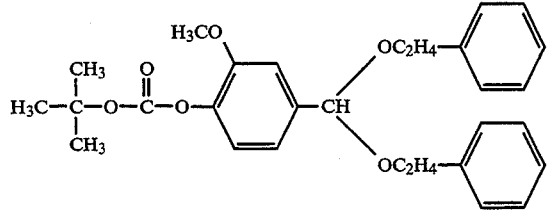

Compound No. 6

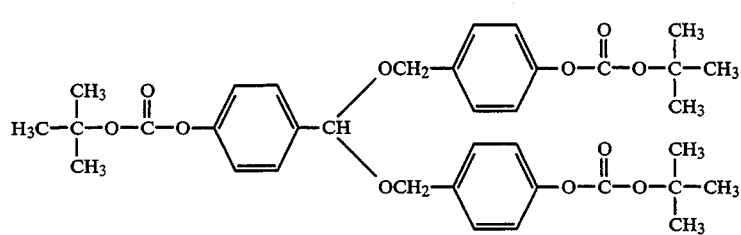

Compound No. 7

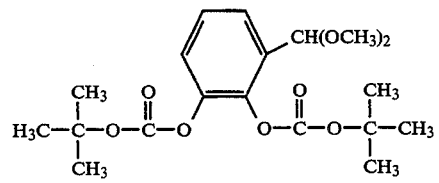

Compound No. 8

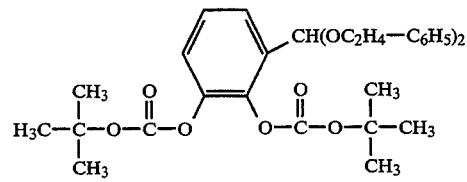

Compound No. 9

EXAMPLES 6 to 44

The compound examples described below were prepared analogously to the instructions given in Example 1 and/or Example 2, only slight changes in the reaction time and working-up being made in individual cases. All the compounds were unambiguously identifiable by elemental analysis, H-NMR and the IR spectrum.

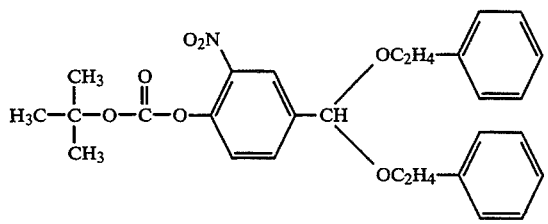

Example No. 6

-continued
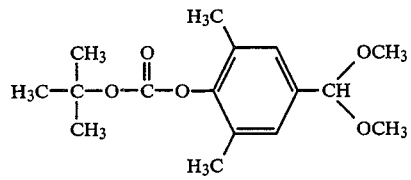 Example No. 7
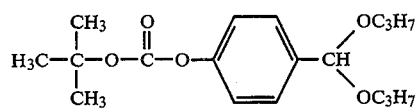 Example No. 8
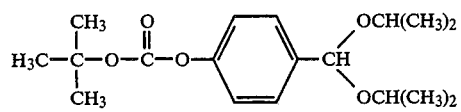 Example No. 9
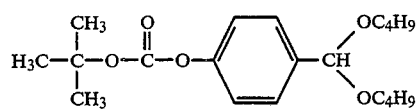 Example No. 10
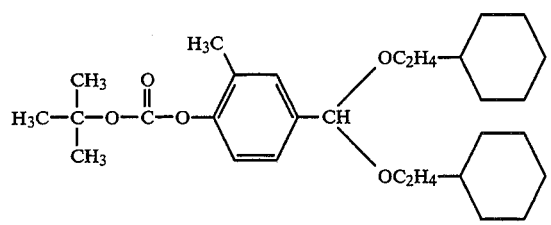 Example No. 11
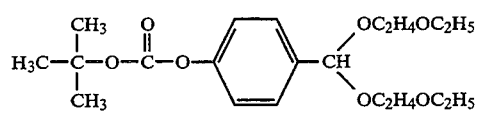 Example No. 12
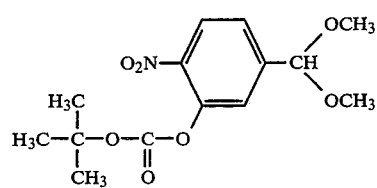 Example No. 13
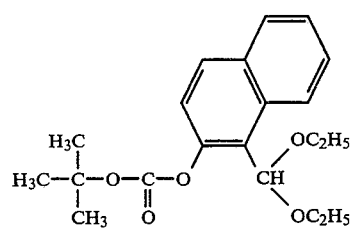 Example No. 14
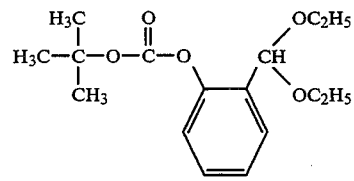 Example No. 15
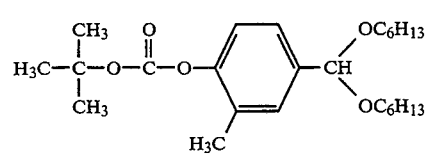 Example No. 16

-continued
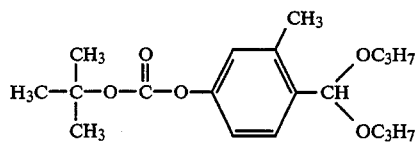
Example No. 17
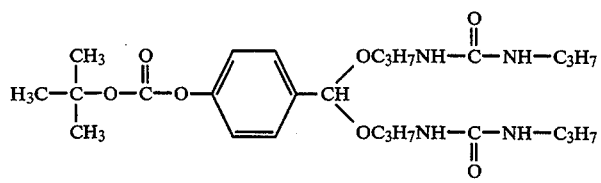
Example No. 18
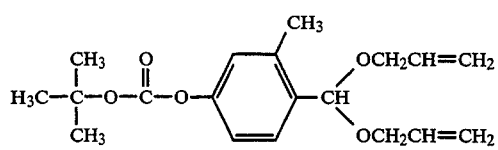
Example No. 19
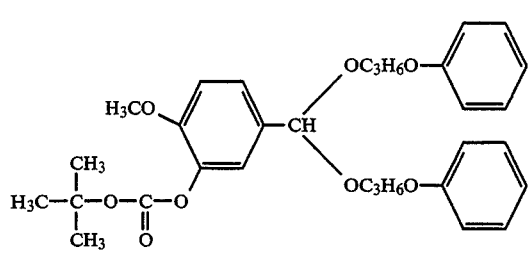
Example No. 20
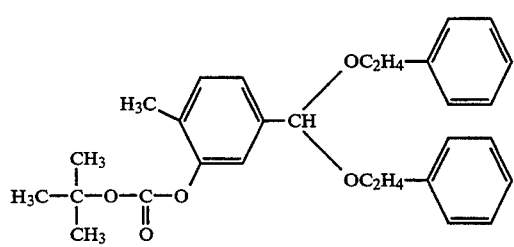
Example No. 21
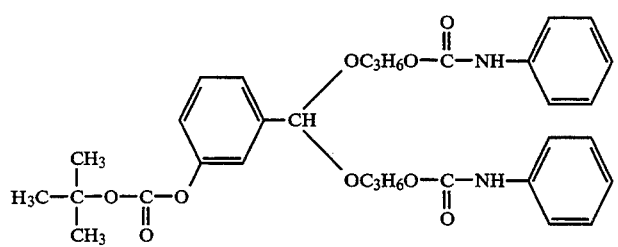
Example No. 22
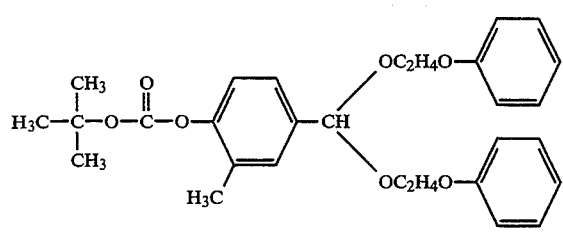
Example NO. 23

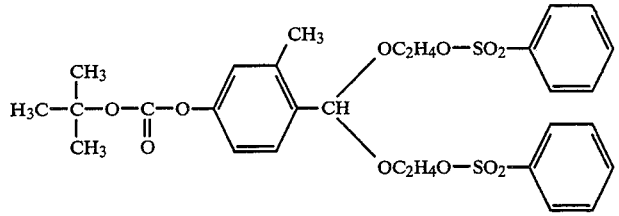
Example No. 24
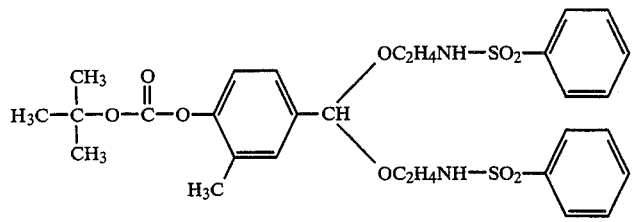
Example No. 25
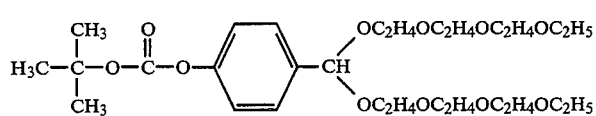
Example No. 26
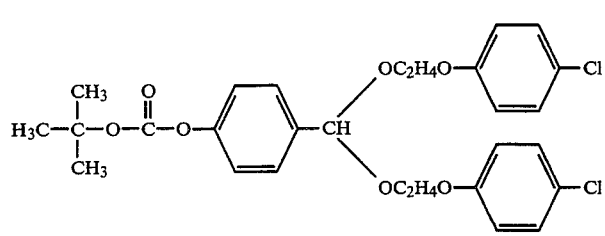
Example No. 27
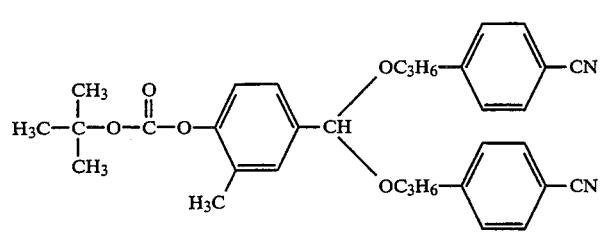
Example No. 28
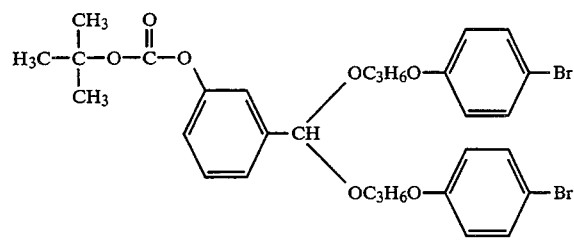
Example No. 29
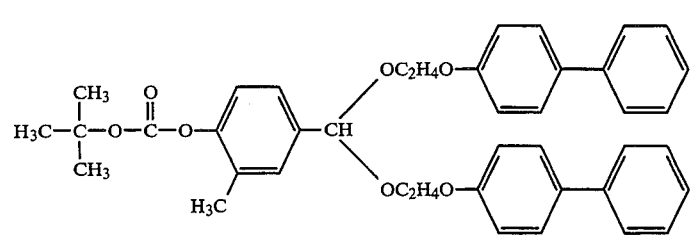
Example No. 30

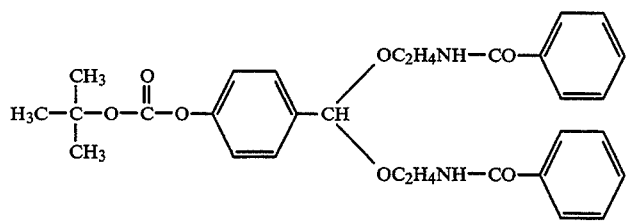
Example No. 31
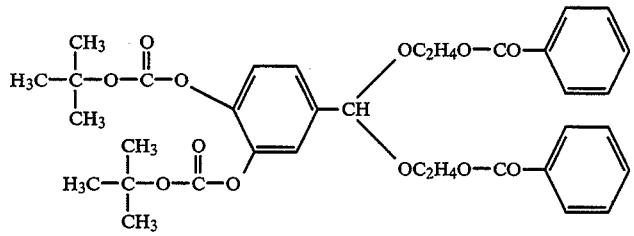
Example No. 32
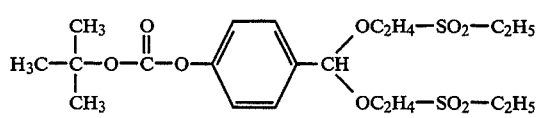
Example No. 33
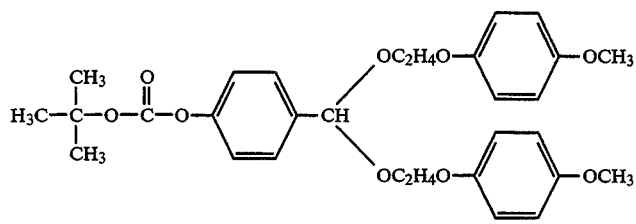
Example No. 34
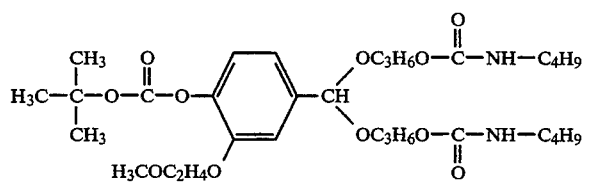
Example No. 35
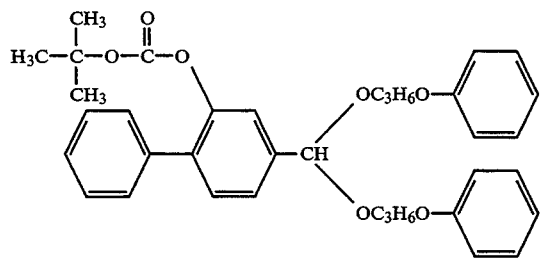
Example No. 36
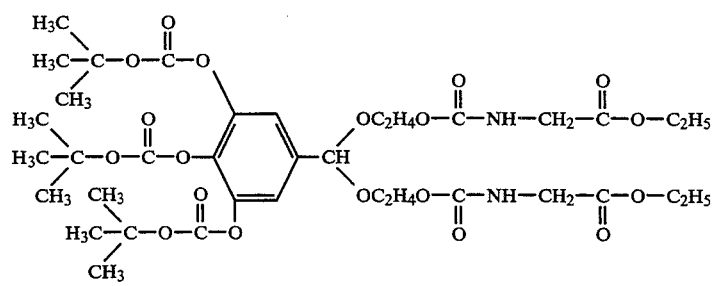
Example No. 37

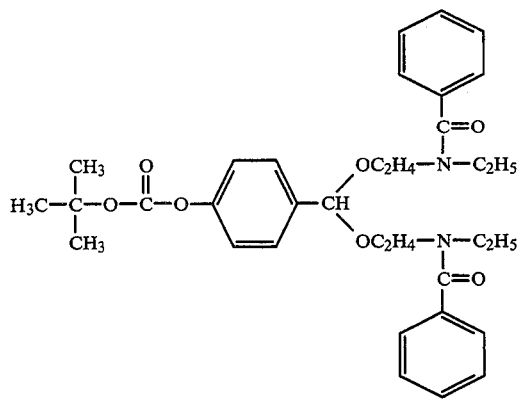
Example No. 38
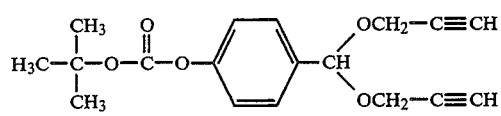
Example No. 39
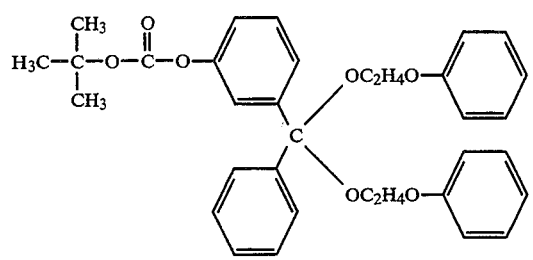
Example No. 40
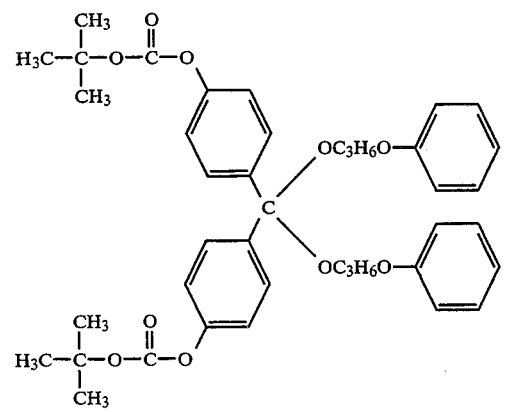
Example No. 41
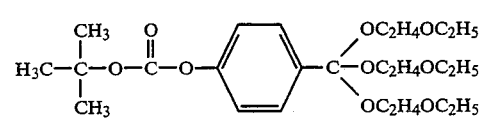
Example No. 42

-continued

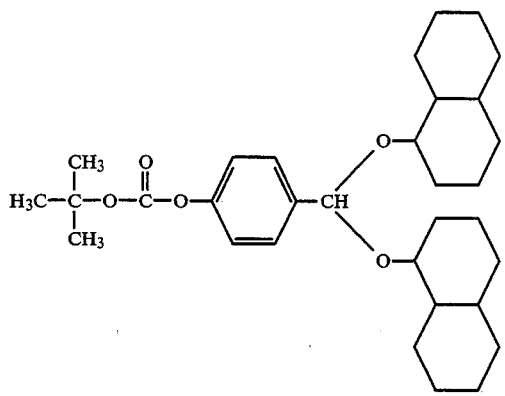

Example No. 43

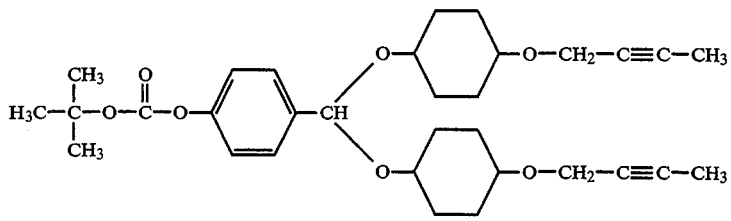

Example No. 44

Application Example 1:

A coating solution was prepared from
- 7.5 p.b.w. of a cresol/formaldehyde novolak having a softening range from 105° to 120° C.,
- 2.0 p.b.w. of 4-tert.-butoxycarbonyloxy-benzaldehyde bis-(2-phenoxyethyl)-acetal,
- 0.4 p.b.w. of 6-(4-chlorostyryl)-4-methyl-1-trifluoromethanesulfonyloxy-2-pyridone and
- 42 p.b.w. of propylene glycol monomethyl ether-acetate.

The solution was filtered through a filter of 0.2 μm pore diameter and whirler-coated at 3,200 rpm onto a wafer treated with an adhesion promoter (hexamethyldisilazane). After drying at 100° C. for 1 minute on the hotplate, a layer thickness of 1.1 μm was obtained.

The recording material was exposed imagewise under an original to the radiation of a xenon/mercury vapor lamp at 365 nm with an energy of 55 mJ/cm². To complete the cleavage of the solubility inhibitor, the material was heated for 1 minute to 100° C.

The recording material was developed with a purely aqueous developer that contained 2.38% by weight of tetramethylammonium hydroxide.

After a developing time of 120 seconds, this gave a perfect image of the mask with steep resist flanks, even structures of less than 0.55 μm being resolved in true detail. An examination of the flanks of the resist profiles by scanning electron microscopy showed that these were aligned virtually perpendicular to the substrate surface. The contrast was 4.6.

The contrast of a positive resist, $c_p$, is defined as $$C_p = 1/(\log D_p - \log D_p^o) = [\log(D_p/D_p^o)]^{-1}$$

where $D_p^o$ is the incident radiation dose at which the developer starts to attack the exposed film, and $D_p$ is the resist reference point (=resist sensitivity). A precise description of this parameter is given in the article by L. F. Thompson and M. J. Bowden "Resist Processing" (Introduction to Microlithography, Theory, Materials and Processing, editors C. G. Willson, L. F. Thompson and M. J. Bowden, ACS Symp. Ser., 219: 164 et seq. (1983), American Chemical Society, Washington).

Application Example 2:

A coating solution was prepared from:
- 7.5 p.b.w. of a copolymer of 3,5-dimethyl-4-hydroxystyrene/4-hydroxystyrene (molar ratio 30:70) having a mean molecular weight of 25,000,
- 2.0 p.b.w. of compound 9 and
- 0.4 p.b.w. of triphenylsulfonium trifluoromethanesulfonate in
- 42 p.b.w. of propylene glycol monomethyl ether-acetate.

The solution was filtered through a filter of 0.2 μm pore diameter and whirler-coated at 3,300 rpm onto a wafer treated with an adhesion promoter (hexamethyldisilazane). After drying for 1 minute at 100° C., a layer thickness of 1.08 μm was obtained.

The recording material was exposed imagewise under an original to the radiation of a xenon/mercury vapor lamp at 240 to 260 nm with an energy of 35 mJ/cm², heated for 75 seconds to 100° C. and then processed using the developer described in Application Example 1.

After a developing time of 60 seconds, this gave a perfect image of the mask with high flank stability. Here again structures of less than 0.4 μm were resolved in true detail.

Application Example 3:

A coating solution was prepared from:
- 7.5 p.b.w. of a copolymer of styrene and maleimide (molar ratio 1:1) having a softening range from 165° to 180° C.,
- 2.0 p.b.w. of compound 4, and
- 0.3 p.b.w. of triphenylsulfonium trifluoromethanesulfonate in
- 42 p.b.w. of cyclohexanone.

The solution was filtered through a filter of 0.2 μm pore diameter and whirler-coated at 3,400 rpm onto a wafer treated with an adhesion promoter (hexamethyldisilazane). After drying for 1 minute at 100° C., a layer thickness of 0.98 μm was obtained.

The recording material was exposed imagewise under an original to the radiation of a xenon/mercury vapor lamp at 240 to 260 nm with an energy of 49 mJ/cm$^2$.

The recording material was developed using a 0.02N aqueous tetramethylammonium hydroxide solution, the exposed areas being detached within 60 seconds without leaving a residue.

This again gave a perfect image of the mask with steep resist flanks. The removal of material in the dark was less than 20 nm; even structures Of less than 0.4 μm were resolved in true detail.

Application Example 4:

A coating solution was prepared from:
7.5 p.b.w. of a homopolymer of 3-methyl-4-hydroxystyrene having a mean molecular weight of 25,000,
2.0 p.b.w. of compound 6, and
0.4 p.b.w. of 4-methyl-6-phenyl-1-trifluoromethanesulfonyloxy-2-pyridone in
42 p.b.w. of propylene glycol monomethyl ether-acetate.

The solution was filtered through a filter of 0.2 μm pore diameter and divided into two equal parts. One part was whirler-coated at 3,300 rpm onto a wafer treated with an adhesion promoter (hexamethyldisilazane). After drying for 1 minute at 100° C. a layer thickness of 1.04 μm was obtained The recording material was exposed imagewise under an original to the radiation of a xenon/mercury vapor lamp at 240 to 260 nm with an energy of 62 mJ/cm$^2$, heated for 75 seconds to 100° C. and then processed using the developer described in Application Example 1.

After a developing time of 60 seconds, this gave a perfect image of the mask with high flank stability. Here again structures of less than 0.4 μm were resolved in true detail.

The second part was subjected to the same procedure after storage in a refrigerator for 20 weeks. Identical results were obtained. This shows that the mixture has extraordinarily good stability in solution.

Application Example 5:

The material described in Application Example 1 was exposed imagewise to radiation of a wavelength of 436 nm. After the processing described in Application Example 1, a correct reproduction of the original down to 0.55 μm was observed.

What is claimed is:

1. A positive-working radiation-sensitive mixture, comprising:
   (a) a compound that generates a strong acid under the action of actinic radiation,
   (b) a compound having at least one C—O—C bond that can be cleaved by the acid generated by the compound (a), said compound represented by the formula I

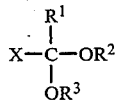

in which

X is a phenyl, (1)naphthyl or (2)naphthyl radical that is substituted by at least one tert.-butoxycarbonyloxy group and optionally by further substituents, $R^1$ is a hydrogen atom, a ($C_1$-$C_6$)-alkyl radical, a ($C_6$-$C_{10}$)-aryl radical or one of the radicals X, and $R^2$ and $R^3$ are identical or different and are a ($C_1$-$C_{12}$)-alkyl radical in which up to three methylene groups are optionally replaced by bridge members having at least one hetero atom, said bridge members being selected from the group consisting of —O—, —S—, —NR$^4$—, —CO—, —CO—O—, —CO—NH—, —O—CO—NH—, —NH—CO—NH—, —CO—NH—CO—, —SO$_2$—, —SO$_2$—O— or —SO$_2$—NH—, a ($C_3$-$C_{12}$)-alkenyl, ($C_3$-$C_{12}$)-alkynyl, ($C_4$-$C_{12}$)-cycloalkyl, ($C_4$-$C_{12}$)-cycloalkenyl and ($C_8$-$C_{16}$)-aralkyl radical, up to three methylene groups of the aliphatic moiety of the ($C_8$-$C_{16}$)-aralkyl radical being optionally replaced by bridge members of the abovementioned type and the aromatic moiety of the ($C_8$-$C_{16}$)-aralkyl radical being optionally substituted by fluorine, chlorine or bromine atoms or by ($C_1$-$C_4$)-alkyl, ($C_1$-$C_4$)-alkoxy, nitro, cyano or tert.-butoxycarbonyloxy groups, $R^4$ being an acyl radical, and (c) a binder that is insoluble in water but soluble or at least swellable in aqueous-alkaline solution.

2. The positive-working radiation-sensitive mixture as claimed in claim 1, wherein $R^4$ is a ($C_1$-$C_6$)-alkanoyl radical.

3. The positive-working radiations-sensitive mixture as claimed in claim 1, wherein X is substituted by a member selected from the group consisting of a fluorine atom, a chlorine atom, a bromine atom, an iodine atom, a nitro group, a cyano group, a carboxyl group, a ($C_1$-$C_9$)-alkyl radical in which up to three methylene groups are optionally replaced by a bridge member as recited in claim 1, a phenyl radical optionally substituted by a member selected from the group consisting of a tert.butoxycarbonyl group, a ($C_1$-$C_4$)alkyl radical, a ($C_1$-$C_4$)-alkoxy radical, a halogen atom, a ($C_8$-$C_{12}$)-aralkyl radical in which up to two methylene groups are optionally replaced by a bridge member as recited in claim 1, a ($C_6$-$C_{10}$)-aryloxy radical, and a ($C_7$-$C_{10}$)-aralkoxy radical.

4. The positive-working radiation-sensitive mixture as claimed in claim 1, wherein X is substituted by a member selected from the group consisting of a fluorine atom, a chlorine atom, a bromine atom, an iodine atom, a nitro group, a cyano group, a carboxyl group, a ($C_1$-$C_6$)-alkyl radical in which up to three methylene groups are optionally replaced by a bridge member as recited in claim 1, a phenyl radical optionally substituted by a member selected from the group consisting of a tert.-butoxycarbonyl group, a ($C_1$-$C_4$)alkyl radical, a ($C_1$-$C_4$)-alkoxy radical, a halogen atom, a ($C_8$-$C_{10}$)-aralkyl radical in which up to two methylene groups are optionally replaced by a bridge member as recited in claim 1, a ($C_6$-$C_{10}$)-aryloxy radical, and a ($C_7$-$C_{10}$)-aralkoxy radical.

5. The positive-working radiation-sensitive mixture as claimed in claim 1, wherein $R^1$ is a hydrogen atom.

6. The positive-working radiation-sensitive mixture as claimed in claim 1, wherein X is a substituted phenyl radical.

7. The positive-working radiation-sensitive mixture as claimed in claim 1, wherein compound (a) generates a sulfonic acid under the action of actinic radiation.

8. The positive-working radiation-sensitive mixture as claimed in claim 1, comprising about 0.25 to 25% by weight of compound (a), relative to the total weight of the solid constituents of the mixture.

9. The positive-working radiation-sensitive mixture as claimed in claim 1, comprising about 0.5 to 15% by weight of compound (a), relative to the total weight of the solid constituents of the mixture.

10. The positive-working radiation-sensitive mixture as claimed in claim 1, comprising about 1.0 to 10% by weight of compound (a), relative to the total weight of the solid constituents of the mixture.

11. The positive-working radiation-sensitive mixture as claimed in claim 1, comprising about 1 to 60% by weight of compound (b), relative to the total weight of the solid constituents of the mixture.

12. The positive-working radiation-sensitive mixture as claimed in claim 1, comprising about 5 to 50% by weight of compound (b), relative to the total weight of the solid constituents of the mixture.

13. The positive-working radiation-sensitive mixture as claimed in claim 1, comprising about 30 to 95% by weight of binder (c), relative to the total weight of the solid constituents of the mixture.

14. The positive-working radiation-sensitive mixture as claimed in claim 1, comprising about 40 to 90% by weight of binder (c), relative to the total weight of the solid constituents of the mixture.

15. The positive-working radiation-sensitive mixture as claimed in claim 1, comprising about 50 to 85% by weight of binder (c), relative to the total weight of the solid constituents of the mixture.

16. A radiation-sensitive recording material, comprising:
a substrate; and
a layer comprising a mixture as claimed in claim 1 coated on said substrate.

17. A positive-working radiation-sensitive mixture as claimed in claim 1, consisting essentially of components (a), (b) and (c).

* * * * *